United States Patent
Müller et al.

(10) Patent No.: US 6,238,386 B1
(45) Date of Patent: May 29, 2001

(54) METHOD AND ARRANGEMENT FOR INVASIVE OR ENDOSCOPIC THERAPY BY UTILIZING ULTRASOUND AND LASER

(76) Inventors: Gerhard Müller, An der Rehwiese 8, 14129 Berlin; Johannes Tschepe, Rosenheimer Strasse 7, 10781 Berlin, both of (DE)

( * ) Notice: Subject to any disclaimer, the term of this patent is extended or adjusted under 35 U.S.C. 154(b) by 0 days.

(21) Appl. No.: 08/211,172
(22) PCT Filed: Jul. 10, 1993
(86) PCT No.: PCT/EP93/01808
§ 371 Date: Mar. 21, 1994
§ 102(e) Date: Mar. 21, 1994
(87) PCT Pub. No.: WO94/02074
PCT Pub. Date: Feb. 3, 1994

(30) Foreign Application Priority Data
Jul. 20, 1992 (DE) ............................................. 42 24 256

(51) Int. Cl.⁷ ................................................. A61B 17/22
(52) U.S. Cl. ............................... 606/10; 606/13; 606/15; 606/17; 600/310; 600/407; 600/411; 600/421; 600/437; 600/439; 600/459; 600/462
(58) Field of Search ........................... 606/2, 3–7, 10–18; 600/310, 407–411, 421, 437–439, 454–464

(56) References Cited

U.S. PATENT DOCUMENTS

| 4,136,700 | * | 1/1979 | Broodwin et al. | 606/169 |
| 4,576,177 | * | 3/1986 | Webster, Jr. | 606/17 |
| 4,587,972 | * | 5/1986 | Morantte, Jr. | 606/17 |
| 4,729,373 | * | 3/1988 | Peyman | 606/4 |
| 4,950,267 | * | 8/1990 | Ishihara et al. | 606/15 |

FOREIGN PATENT DOCUMENTS

| 3935528 | 5/1991 | (DE) . | |
| 4103145 | 8/1992 | (DE) . | |
| 4115447 | 11/1992 | (DE) . | |
| 189329 | * 7/1986 | (EP) | 606/7 |
| 0329492 | 8/1989 | (EP) . | |
| WO 85/00510 | 2/1985 | (WO) . | |
| WO 87/01269 | 3/1987 | (WO) . | |

* cited by examiner

Primary Examiner—David M. Shay
(74) Attorney, Agent, or Firm—Walter Ottesen

(57) ABSTRACT

Sound energy of a proximally arranged sound source 30 and laser radiation of a therapeutic laser 17 are simultaneously transmitted with an endoscopic instrument via flexible waveguides 3 into the body interior. The sound energy is in a power and frequency range adequate for the cutting tissue 16 and the therapeutic laser 7 operates preferably in the near infrared. The waveguides are quartz glass fibers 3 which can transmit sound energy as well as also light energy.

15 Claims, 7 Drawing Sheets

METHOD AND ARRANGEMENT FOR INVASIVE OR ENDOSCOPIC THERAPY BY UTILIZING ULTRASOUND AND LASER

BACKGROUND OF THE INVENTION

In medicine, ultrasonic technology has become established in diagnostics as well as in therapy. Ultrasound is utilized in diagnostics in laparoscopy and angioplasty in addition to the known extracorporeal image yielding methods. For example, plaque in arteries is diagnosed with an ultrasonic catheter in the high frequency ultrasonic range between 5 MHz and 40 MHz.

Lower frequency energy ultrasound between 20 and 40 kHz is used for cutting tissue in open surgery. For example, the so-called CUSA-technique (Cavitation Ultrasonics Surgical Aspirator) is preferably used for the excision of brain and liver tumors in neurosurgery and in general surgery. The advantage of the CUSA-method is seen in the tissue-differentiating cutting. This is so because the soft tumor cells can be separated without much blood loss while the elastic organ supplying vessels and nerves are spared.

However, up until now, there is no endoscopically useable applicator having an amplitude adequate for cutting tissue. The metal sound conductors used until now have losses which are too high with the result of an intense development of heat in the sound conductor which is unwanted for endoscopic applications. Metal hollow waveguides and corresponding applicators for ultrasonic angioplasty are known and are, for example, described in the dissertation paper of U. Stumpf "Die Erzeugung und Ubertragung von Ultraschalldehnwellen hoher Energiedichten in flexiblen Wellenleitern im 20 kHz-Bereich fur therapeutische Anwendungen" (RWTH Aachen, 1978).

It is known from International patent application publication no. WO 87/01269 to utilize flexible glass fibers as sound conductors for an image-forming ultrasonic diagnostic method. In this method, however, only relatively low sound energies are transmitted via the waveguide.

From the older, but yet not published patent application DE 41 15 447 as well as patent application DE 41 03 145, it is known to transmit ultrasound, for example, with the aid of quartz glass fibers into the interior of the body, first to monitor the degree of destruction of the concrements during the extracorporeal shock wave lithotripsy and, on the other hand, for example, for the medical endosonography. In both cases, however, likewise only a relatively low sound energy is transmitted by the quartz glass waveguide. Insofar as the transmission of optical signals or light energy is touched upon in the above-mentioned DE 41 03 145, only low radiation intensities are concerned here as they are required, for example, for illuminating the object sighted by the endoscope.

Furthermore, it is known to transmit high intensity light or laser radiation via optical light waveguides, especially also made of quartz glass, and to use this radiation, for example, with the aid of endoscopes and catheters for cutting and coagulating tissue in the interior of the body.

The two methods touched upon, the ultrasound therapy according to the, for example, CUSA-technique and the laser surgery have previously, however, been alternatively used in dependence upon whether the one or the other method is better suited for the desired purpose. A combination of both methods is not known up to now.

From DE-OS 39 35 528, it is known to transmit the radiation of a pulsed laser for the treatment of biological tissue and, at the same time, to conduct back the shock waves occurring distally during the treatment via the quartz glass fibers to a pressure receiver coupled proximally to the fiber. This known system is, however, neither suited for ultrasound therapy nor for the ultrasound diagnosis.

SUMMARY OF THE INVENTION

It is the object of the present invention to provide a method and an arrangement with which ultrasonic energy as well as laser energy can be transmitted simultaneously, that is, during one and the same treatment operation, into the interior of the body.

According to the invention, laser energy, preferably in the near infrared range, and ultrasound are simultaneously transmitted via waveguides into the interior of the body with the power adequate for the particular medical application and in the suitable frequency range. In this way, it becomes possible to combine the advantages of the two methods with each other and to cut tissue, for example, with ultrasound in a very tissue differentiating manner while at the same time or alternately to coagulate the cut edges with the aid of the laser radiation in order to prevent bleeding. On the other hand, it is also possible to utilize the laser selectively to cut the tissue parts which cannot be cut ultrasonically or only with difficulty. In this way, new innovative treatment methods in the context of minimally invasive medicine are obtained.

According to a further embodiment of the invention, it is also possible to conduct ultrasound via the waveguides from the distal end back to a proximal receiver and therefore use the instrument additionally for diagnosis for ultrasound monitoring in accordance with the so-called A-scan method. This A-scan method is a one-dimensional display method wherein acoustic energy is transmitted from a fixed sound head to the body region to be investigated. The part of the sound wave reflected at each interface is again received by the sound head so that with the known speed of sound, the distance to the reflection location can be computed from the travel time and displayed on a monitor. In this manner, moving interfaces are detected by the amplitudes that shift on the time axis. (E. Krestel "Bildgebende Systeme fur die medizinische Diagnostik" published 1980, Siemens AG Press, second edition, 1988).

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
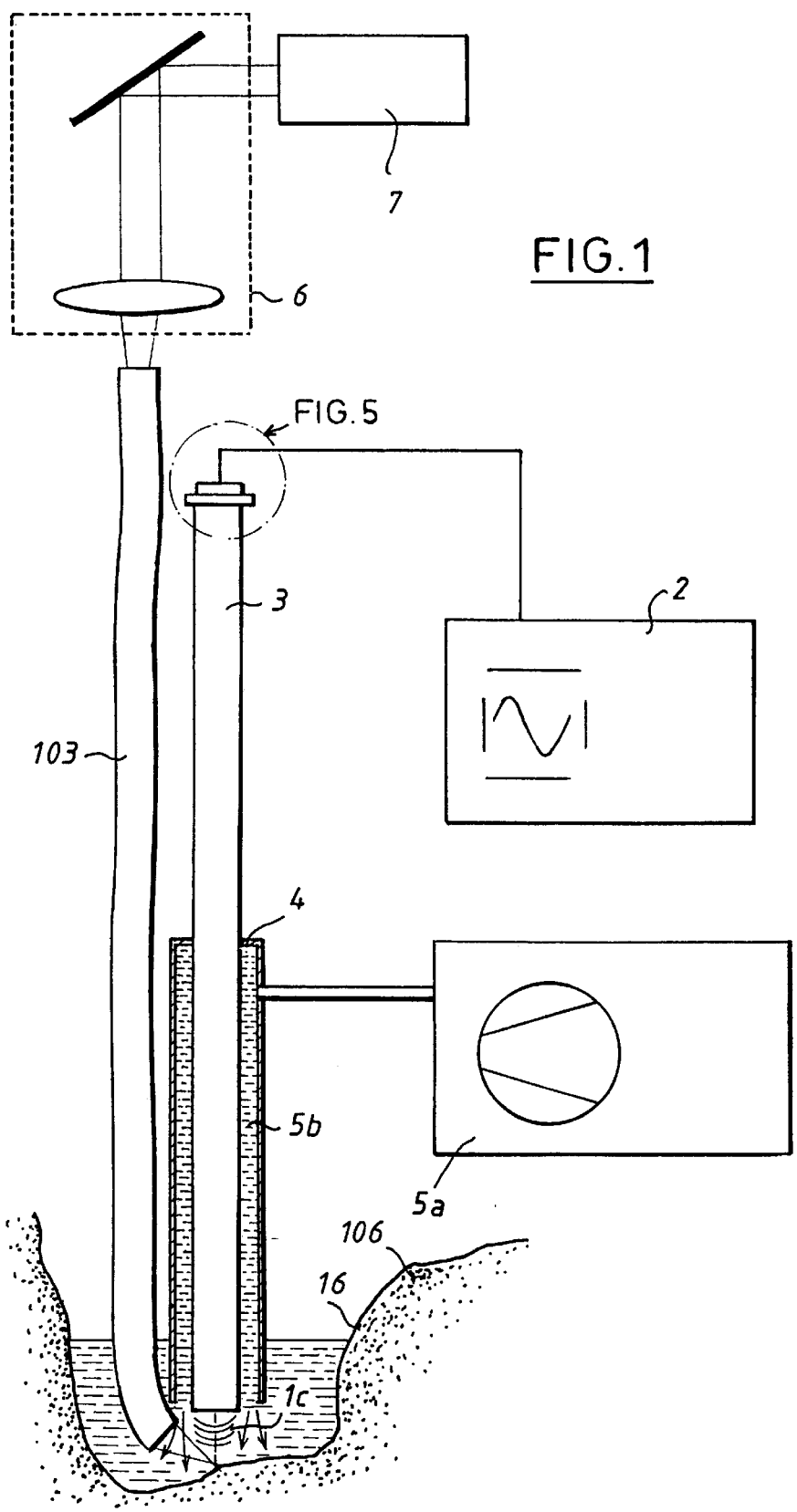
FIG. 1 is an assembly of a first embodiment of the instrument of the invention in a greatly simplified schematic illustration.

FIG. 1 shows schematically the configuration of the instrument of the invention according to a first embodiment. The waveguide 3 is a plastic-coated flexible quartz glass fiber as it can be obtained, for example, from the Ensign Bickford Optic Company under the designation HCP-fiber. The waveguide 3 is coupled at the proximal end to the ultrasonic transmitter shown in detail in FIG. 5. The ultrasonic transmitter is electrically connected to a drive circuit 2. A likewise flexible thin coaxial jacket 4 surrounds the quartz glass fiber. The quartz glass fiber is flushed with a liquid medium 5b within this jacket 4 and the liquid medium 5b is supplied by an irrigator unit 5a. The liquid medium is, for example, glycerol (85%). The liquid exits from the jacket 4 at the distal end of the quartz glass fiber 3 and serves there as an acoustic immersion liquid which produces the acoustic contact between the end of the quartz glass fiber 3 and the body tissue 16 onto which the ultrasonic energy 1c is directed. At the same time, the liquid in the jacket 4 cools the quartz glass fiber 3.

A second waveguide 103, which is likewise a quartz glass fiber, is arranged next to the waveguide 3. The beam of a therapeutic laser 7 is transmitted via this second waveguide 103 and is deflected via an optic 6, focused on the proximal entry end of the fiber 103 and is transmitted to the distal end of the instrument. The laser radiation exiting at the distal end impinges on the tissue 16 directly in front of the waveguide 3 which transmits the ultrasonic energy.

The laser 7 is a therapeutic laser which radiates in the wavelength range between 300 nm and 3 µm, preferably in the near infrared between 1 µm and 1.5 µm, and is, for example, an Nd:YAG-laser. The quartz fibers (103 and 3) both have a diameter of at least 0.1 mm and in the illustrated embodiment 0.5 mm. The quartz fibers (103 and 3) are suitable for transmitting light energy with a power of at least 5 Watts to the distal end. This power is such as is required for coagulating tissue. The quartz fibers are likewise capable of transmitting ultrasonic energy of at least 5 Watts to the distal end as is necessary for cutting and disintegrating soft tissue. This energy is in a frequency range of less than 1 MHz and preferably between 30 kHz and 200 kHz.

The tissue 16, for example a tumor, is disintegrated by the ultrasonic energy 1c and is drawn off by suction via the irrigation channel present in the endoscope (not shown) while, at the same time, the cut edges remaining to the healthy tissue are coagulated with the laser 7 activated during the treatment.

Figure 5:
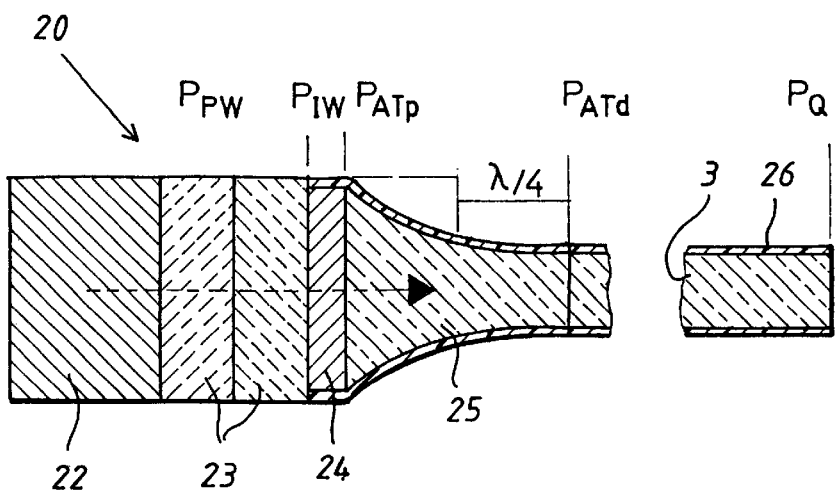
FIG. 5 is a more detailed sketch of the sound head used for the instruments of FIGS. 1 and 3.

In FIG. 5, the sound head 20, which is seated on the proximal end of the waveguide 3, is shown in more detail. The sound head comprises a damping member 22 in the form of a steel disc, a sound transducer placed forward of the steel disc in the form of two discs 23 of piezoceramic material, an impedance converter 24 in the form of a disc which is likewise cylindrical and made of a material having characteristics which are determined below as well as an amplitude transformer 25 in the form of a taper. The amplitude transformer 25 provides the transition from the diameter of the sound transducer, which is larger in cross section, to the smaller diameter of the waveguide 3 placed against the amplitude transformer. The amplitude transformer 25 increases the deflection of the piezoceramic, which is less because of the yield point, to the greater longitudinal amplitude deflection of the quartz waveguide 3. The amplitude transformer 25 likewise comprises quartz glass. The amplitude transformer 25 is configured as a sound horn and has an exponential form which causes the excursion amplitude of the ultrasonic wave to increase inversely proportionally to the diameter of the amplitude transformer. The ultrasonic wave is generated by the piezoceramic discs 23. Reference numeral 26 identifies the plastic layer which usually jackets commercially available quartz glass fibers.

The distal maximum permissible amplitude of the deflection for the quartz glass waveguide can be computed: PQ $$S = \frac{P_Q}{D_Q \times C_Q \times 2\pi f} \quad (1)$$

wherein:

$P_Q$ is the maximum tensile stress in quartz;
$C_Q$ is the velocity of sound in quartz;
$D_Q$ is the specific density of the quartz; and,
f is the frequency of the ultrasound.

In order to realize a distal deflection amplitude adequately high for the ultrasound therapy, the deflection of the ceramic discs 23 must be increased by the amplitude transformer 25. The deflection of the ceramic discs 23 is smaller because of the yield point. If the amplitude transformer 25 has an exponential form, then the deflection amplitude increases inversely proportionally to the diameter.

For dimensioning the amplitude transformer, it is assumed that the narrow part of the transformer piece is $\lambda/4$ long so that the jump in cross section lies in the stress bulge.

Accordingly, the following applies:

$$P_{ATd} = \frac{D_{ATd} \times C_{ATd}}{D_Q \times C_Q} P_Q \quad (2)$$

wherein:

$D_{ATd}$ is the density of the amplitude transformer; and,
$C_{ATd}$ is the velocity of sound in the amplitude transformer.

Since the waveguide 3 as well as the amplitude transformer 25 are made of quartz glass, the stress value of the narrow part can be computed from equation (1).

The following applies for the ratio e of the cross-sectional surfaces:

$$P_{ATp} = \epsilon\, P_{ATd} \quad (3)$$

wherein:

$P_{ATp}$ is the tensile stress of the amplitude transformer at the proximal end; and,
$P_{ATd}$ is the tensile stress of the amplitude transformer at the distal end.

For the yield point of the impedance converter PIW' the following then results:

$$P_{IW} = \frac{D_{IW} \times C_{IW}}{D_Q \times C_Q} \epsilon P_Q \quad (4)$$

wherein:

$D_{IW}$ is the density of the impedance converter 24; and,
$C_{IW}$ is the velocity of sound in the impedance converter 24.

From the above, the yield point of the sound transducer Ppw is:

$$P_{PW} = \frac{D_{PW} \times C_{PW}}{D_{IW} \times C_{IW}} P_{IW} = \frac{D_{PW} \times C_{PW}}{P_Q \times C_Q} \epsilon P_Q \quad (5)$$

wherein:

$D_{PW}$ is the density of the sound transducer 23; and,
$C_{PW}$ is the velocity of sound in the sound transducer 23.

Since $P_{PW}$ however is initially pregiven as the material constant, $\epsilon$ can be computed as follows:

$$\epsilon = \frac{P_{PW} \times D_Q \times C_Q}{P_Q \times D_{PW} \times C_{PW}} \quad (6)$$

In this way, the amplitude transformer is dimensioned.

The sound wave travels from the ceramic discs 23 in the direction of the quartz glass waveguide 3. An impedance adaptation is necessary so that there are minimal reflection losses at the interface between the ceramic and quartz. For this purpose, the impedance converter 24 is computed in the following.

A $\lambda/4$ impedance adaptation is formulated as follows: $Z_X = D_X C_X$ is the mechanical impedance of the material x. Then, for perpendicular incidence of sound, the impedance of the impedance converter is:

$$Z_{IW} = \sqrt{Z_Q \times Z_{PW}} \quad (7)$$

and for its length $l_{IW}$:

$$l_{IW} = \frac{\lambda}{4} = \frac{C_{IW}}{4f} \quad (8)$$

A suitable impedance converter material must be selected based on the computed impedance. For this purpose, glass of appropriate composition, ceramic or metal are suitable. However, in this context, it must be considered that the yield point of equation (1) is not exceeded.

For optimal $\lambda/4$ adaptation, the reflection factor of the entire system vanishes and the incident energy is completely transmitted by the piezoceramic discs 23 to the waveguide 3 while disregarding internal losses.

The following is to be considered for the geometric dimensioning.

With the materials pregiven, the yield points of the waveguide 3, amplitude transformer 25 and sound transducer 23 are known.

The yield point of quartz is: $P_Q = 20-30 \cdot 10^7$ Pa and the yield point of ceramic is: $P_{PW} = 12.5 \cdot 10^7$ Pa.

Furthermore, the density D and the sound velocity $C_L$ for the longitudinal waves for quartz ($D_Q$ and $C_{LQ}$) and for ceramic ($D_P$ and $C_{LP}$) are pregiven.

The following remain as free parameters:
(i) the distal diameter of the waveguide dd and
(ii) the frequency f or the deflection s at the distal end of the waveguide.

For a waveguide of quartz glass having a diameter of 1 mm while utilizing piezoceramic discs of 2.4 mm diameter, at a frequency of 25 kHz, deflection amplitudes of 0.15 mm at the distal end of the waveguide 3 are obtained for the sound transducer when the following values for the impedance and tensile stresses are assumed to be given:

$Z_Q = 1.33 \cdot 10^7$ kg/m$^2$ s, $P_{PW} = 1.25 \cdot 10^8$ Pa, $P_Q = 3 \cdot 10^8$ Pa, $Z_{IW} = 2.07 \cdot 10^7$ kg/m$^2$ s, $Z_{PW} = 3.12 \cdot 10^7$ kg/m$^2$ s, $P_{IW} = 8.4 \cdot 10^7$ Pa.

This corresponds to a theoretically obtainable sonic power of 2.6 kW at the distal end of the waveguide 3. Such a sonic power is more than adequate for cutting tissue. At higher frequencies, the maximum obtainable deflection amplitude is correspondingly lower because of the yield point.

Figure 2:
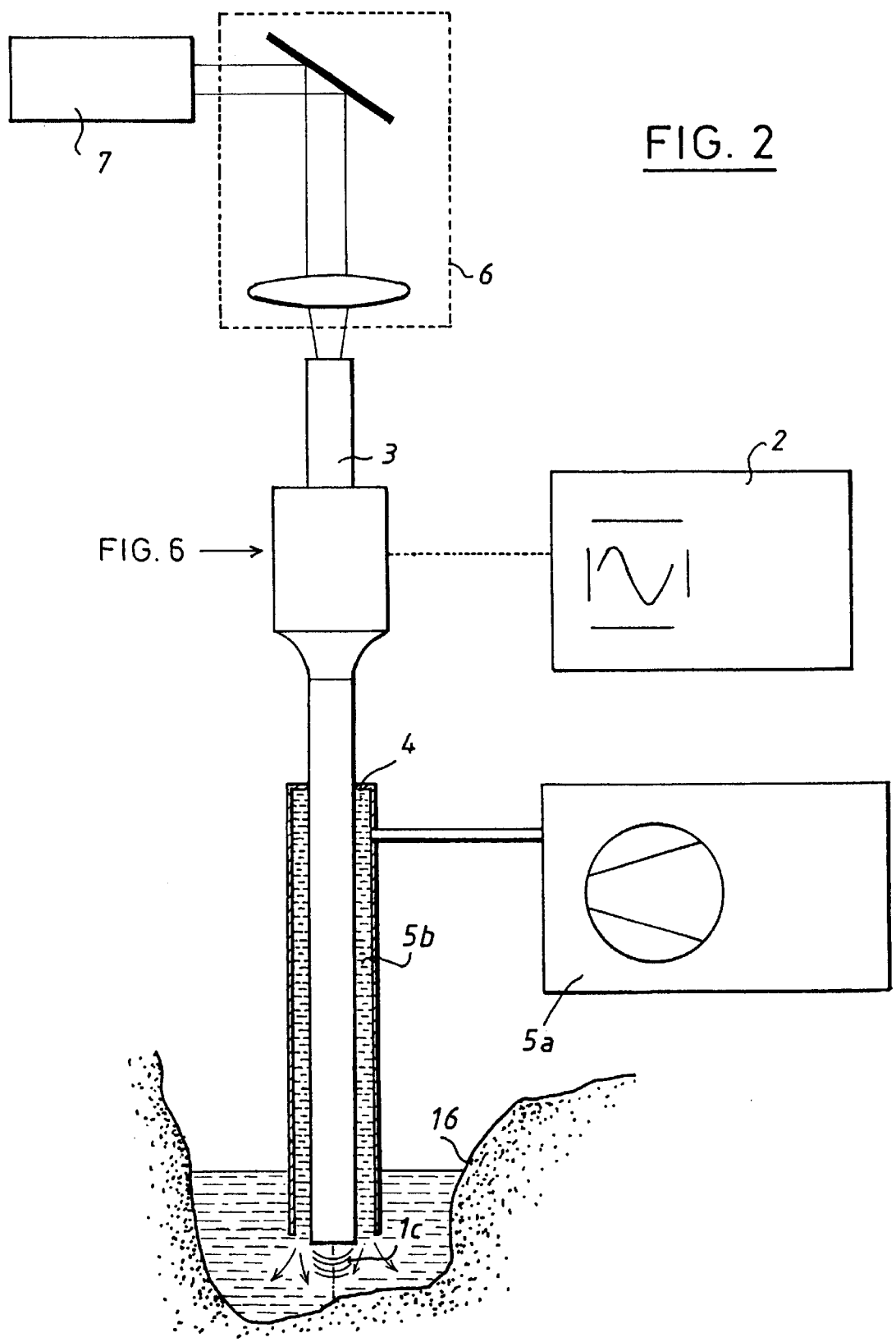
FIG. 2 is a modified variant of the instrument of FIG. 1.

In FIG. 2, an alternate embodiment of the instrument of FIG. 1 is shown. According to this second embodiment, ultrasonic radiation and laser radiation are transmitted by the same waveguide and are directed onto the tissue 16 at the distal end. For this purpose, the laser radiation supplied by the laser generator 7 is coupled by the deflecting and focusing optics 6 into the proximal end of the waveguide 3 and the ultrasound generator 2 is connected to an annularly-shaped ultrasonic head 30 which is shown in greater detail in FIG. 6. The annularly-shaped ultrasonic head 30 surrounds the waveguide. The remaining components correspond to those in the embodiment of FIG. 1 and are therefore not explained here again.

Figure 6:
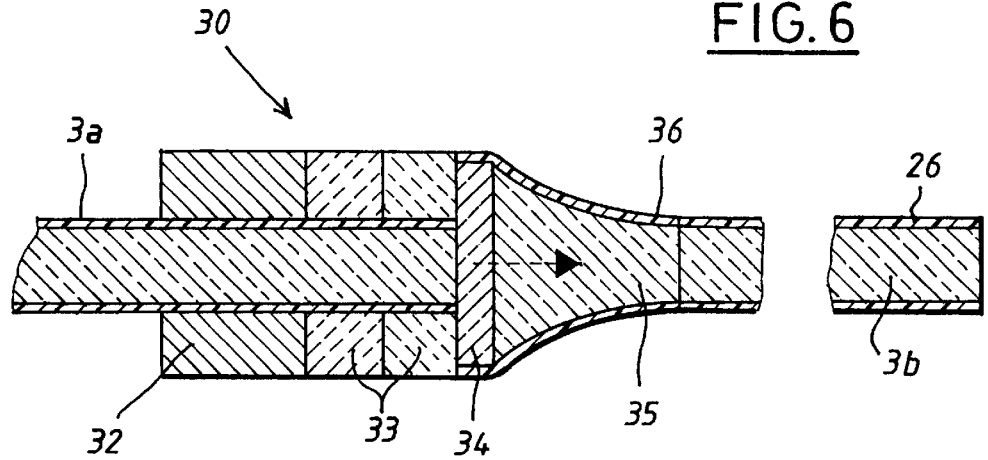
FIG. 6 is a more detailed sketch of the sound head used for the instruments of FIGS. 2 and 4.

As shown in FIG. 6, the waveguide 3 is partitioned in the region of the ultrasonic head 30. The proximal component piece 3a of the quartz glass waveguide is seated in a coaxial bore of the ultrasonic head and this bore extends through the damping element 32 and the piezoceramic discs 33 of the sound transducer and terminates at the impedance converter 34 which, in this case, comprises glass transparent for the wavelength of the laser 7. The amplitude transformer 35, which follows after the impedance converter 34, as well as the following waveguide 3b comprise quartz glass as in the embodiment of FIG. 5.

The impedance converter 34 and the amplitude transformer 35 as well as the waveguide 3 are provided with an optical cladding 36 in order to prevent the exiting of laser light. The cladding 36 can be a hard polymer applied, for example, in an immersion method as it is used commercially for so-called HCP (Hard Clad Plastic) fibers.

With the applicator shown in FIG. 2, ultrasonic radiation and laser radiation are directed, simultaneously or intermittently, via the same waveguide 3 onto the tissue 16 to be treated so that, for example, soft tissue is cut with ultrasound and is simultaneously coagulated with the Nd:YAG laser 7. Furthermore, the data provided for FIG. 1 with respect to the dimensioning of the fiber, the laser power and sonic power transmitted and the frequency range or wavelength ranges used apply in the same manner for the instrument of FIG. 2 or FIG. 6.

Figure 9:
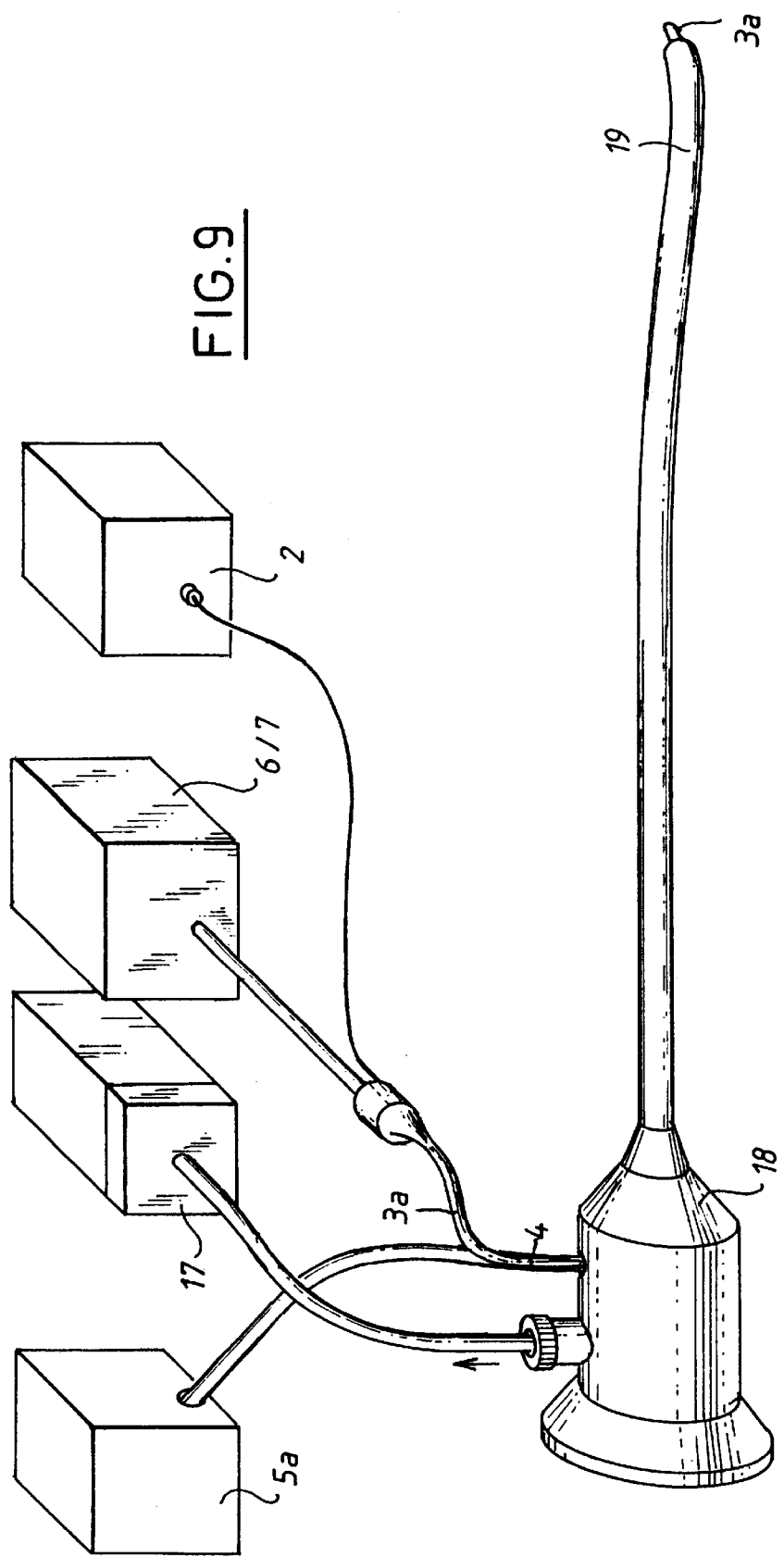

The waveguide 3a can, for example, be mounted in the treatment channel of the endoscope 18 shown in FIG. 9. This endoscope makes possible the guidance and positioning of the waveguide at the treatment location in the particular opening in the body. Insofar as the endoscope is a flexible endoscope, the endoscope has the required devices to move or bend the distal end 19. The endoscope furthermore includes the necessary channels and pump device 17 with which the liquid 5b, which is supplied via the jacket 4, can be drawn off by suction.

Figure 3:
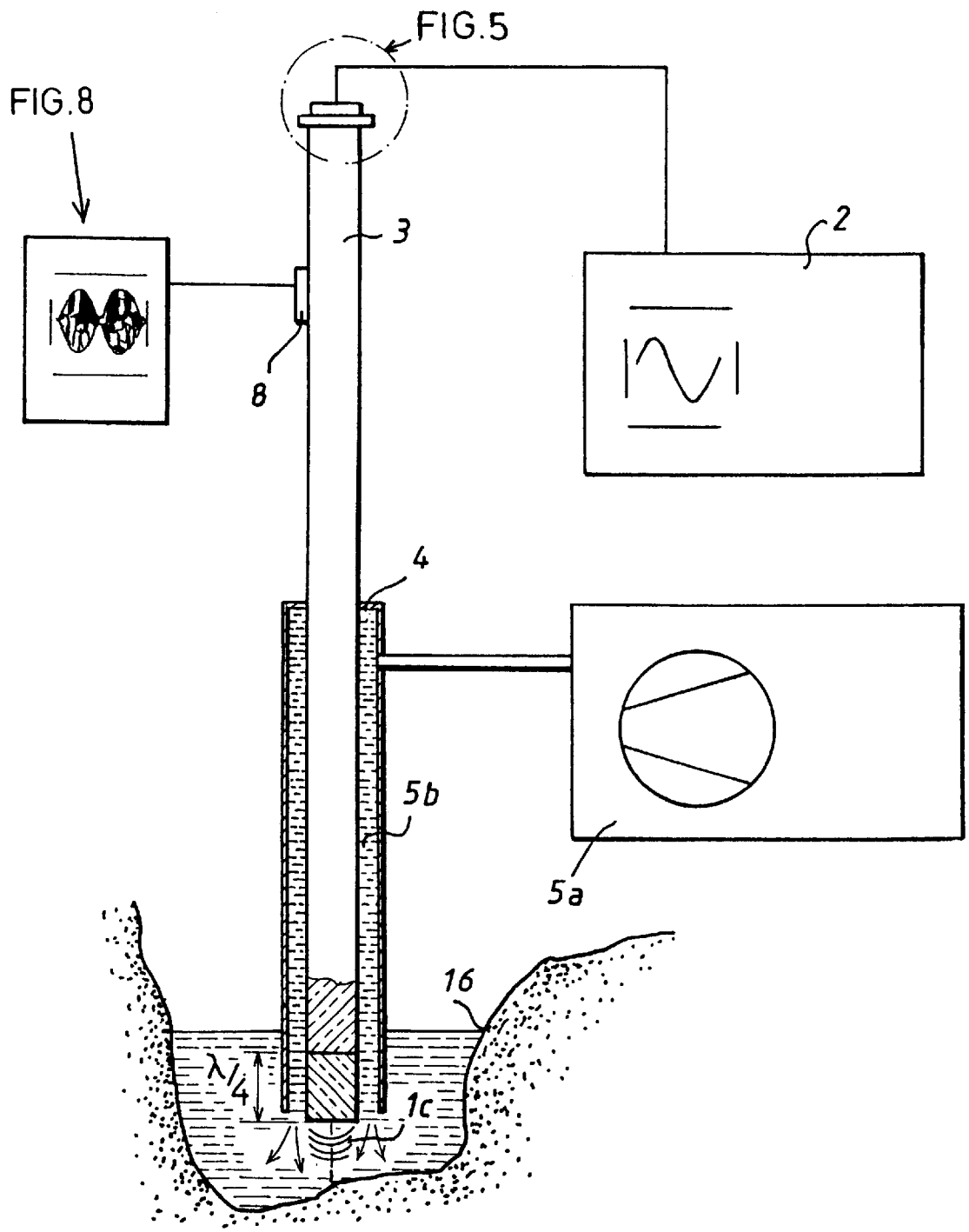
FIG. 3 is another embodiment of the instrument according to the invention.

In FIG. 3, the waveguide 3 of FIG. 1 is equipped with an additional signal transducer and receiver 8 for ultrasonic measuring signals for measuring tissue layers pursuant to the so-called A-scan method. Ultrasound signals of low power are generated with the signal transducer and receiver 8 and are transmitted via the waveguide 3 to the distal end. The sonic power for the diagnosis lies under 1 Watt and the sound intensity at the distal end amounts to less than 100 Watts/cm$^2$ in order to preclude damage to tissue. However, an ultrasonic frequency of a magnitude of greater than 1 MHz is used for the diagnosis with the ultrasonic frequency going up to 50 MHz and preferably being between 1 and 10 MHz.

Figure 8:
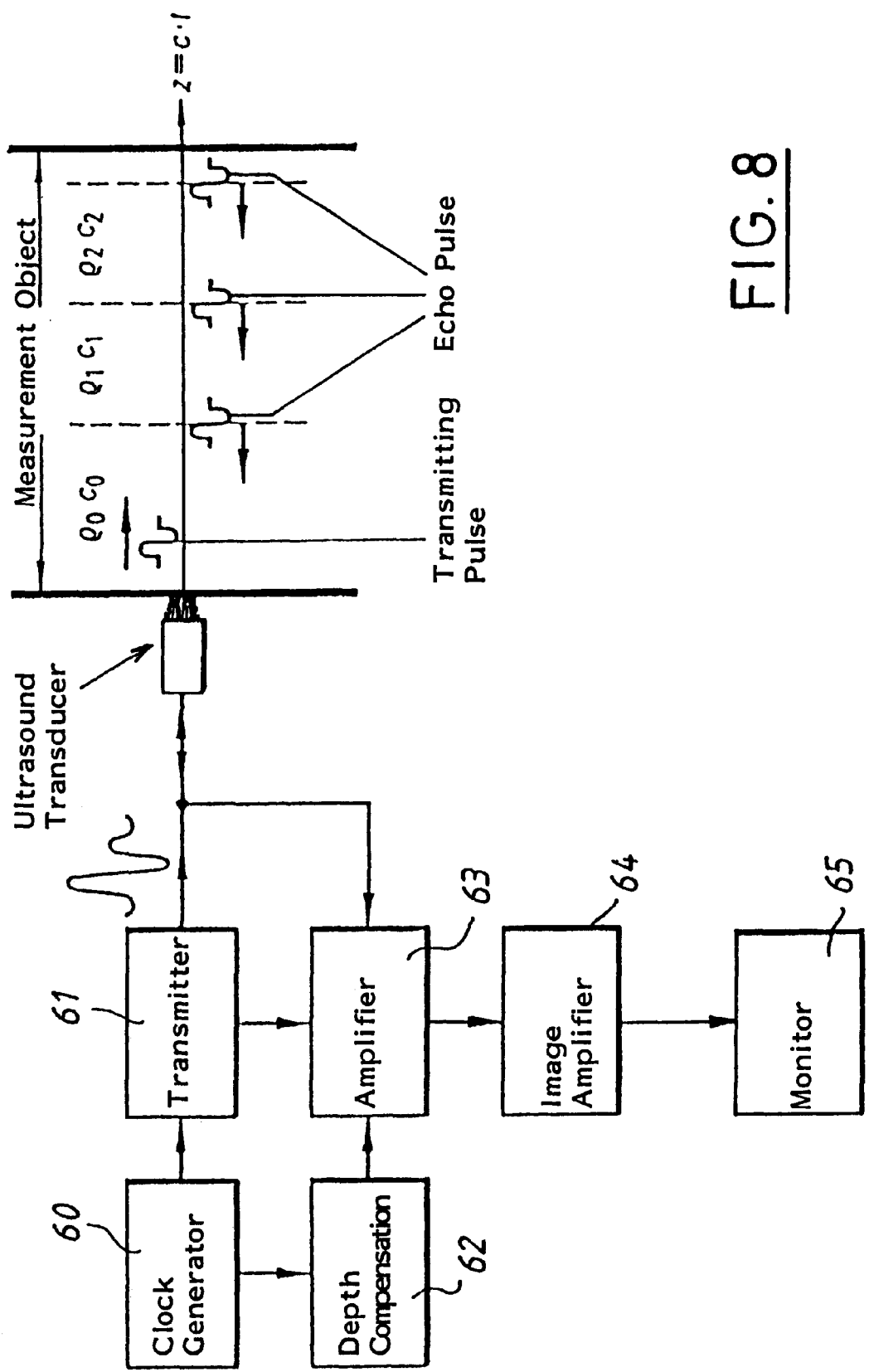
FIG. 8 is a block circuit diagram of the electronics for the ultrasound diagnostic part of the instrument of FIG. 3; and, FIG. 9 is a simplified sketch showing the use of the instrument of the invention in combination with an endoscope.

The so-called A-scan method is a one-dimensional display method. Here, acoustic energy from the transducer 8 is transmitted via the waveguide 3 into the region of the body to be investigated. At each interface, a portion of the sound waves is reflected. The wave travelling back through the waveguide 3 is again received by the sound transducer 8. For known sound velocity, the distance of the reflecting location can be computed from the travel time. The received signals can then be, for example, displayed on a monitor. Here, a point travels on the monitor on the x-axis and a clock signal controls the image tube in such a manner that the start of the point movement is coincident in time with the reception of the reflected sound signal. The point travel time can be so adjusted that the distances of the reflecting locations, for example, organ interfaces, can be read directly from the monitor. Reflected signals are displayed by an amplitude on the y-axis with the amplitude being proportional to a sound intensity. The sound wave intensities become less with increasing depth of penetration. With the aid of a time-dependent amplification, later arriving signals are more amplified in order to compensate for intensity losses in the tissue. Moving interfaces are detectable by the amplitudes shifting on the time axis (x-axis). The measuring transmitter electronics and evaluation electronics 9 required for this purpose is shown in greater detail in the block circuit diagram of FIG. 8. In FIG. 8, reference numeral 60 identifies the clock generator, 61 the ultrasound transmitter, 63 the amplifier for the received signals, 62 the electronics for the depth compensation which controls the amplification factor as a function of time, 64 the image amplifier and 65 the monitor on which the signals are displayed.

If ultrasonic diagnosis is performed additionally with the instrument of FIG. 3, then the reflection losses caused by the impedance jump at the distal end of the waveguide 3 are to be considered. The losses during initial radiation can still be compensated by an increase of the transmitting power. However, this is no longer possible for the return-travelling echo signal because then a still higher transmitting power would have to be transmitted to the distal end which would unnecessarily stress the tissue or a signal loss must be accepted. For this reason, an impedance adaptation is necessary for the ultrasonic diagnosis via a quartz glass fiber. The large impedance jump from $13.3 \times 10_6$ $kgm^{-2}$ $s^{-1}$ for quartz glass to 0.5 to $1.7 \times 10^6$ $kgm^{-2}$ $s^{-1}$ for typical soft tissues amplifies this requirement further. Intensity losses between 60 and 85% when transmitting and receiving would have to be expected here.

The irrigating liquid transmitted via the jacket 4 can, in principle, be used for the impedance adaptation; however, it is problematical to obtain correspondingly high impedances between 2.5 to $4.5 \times 10^6$ $kgm^{-2}$ $s^{-1}$. Furthermore, the layer thickness of the irrigating liquid is not easily held constant at the value of $\lambda/4$ required for the impedance adaptation. For this reason, an impedance converter in the form of a suitable glass having an impedance of approximately $4 \times 10^6$ $kgm^{-2}$ $s^{-1}$ is placed on the distal end of the waveguide 3. This impedance converter 109 is connected sound tight to the quartz glass fiber 3, for example, with adhesive, splicing or form-tight techniques.

Figure 4:
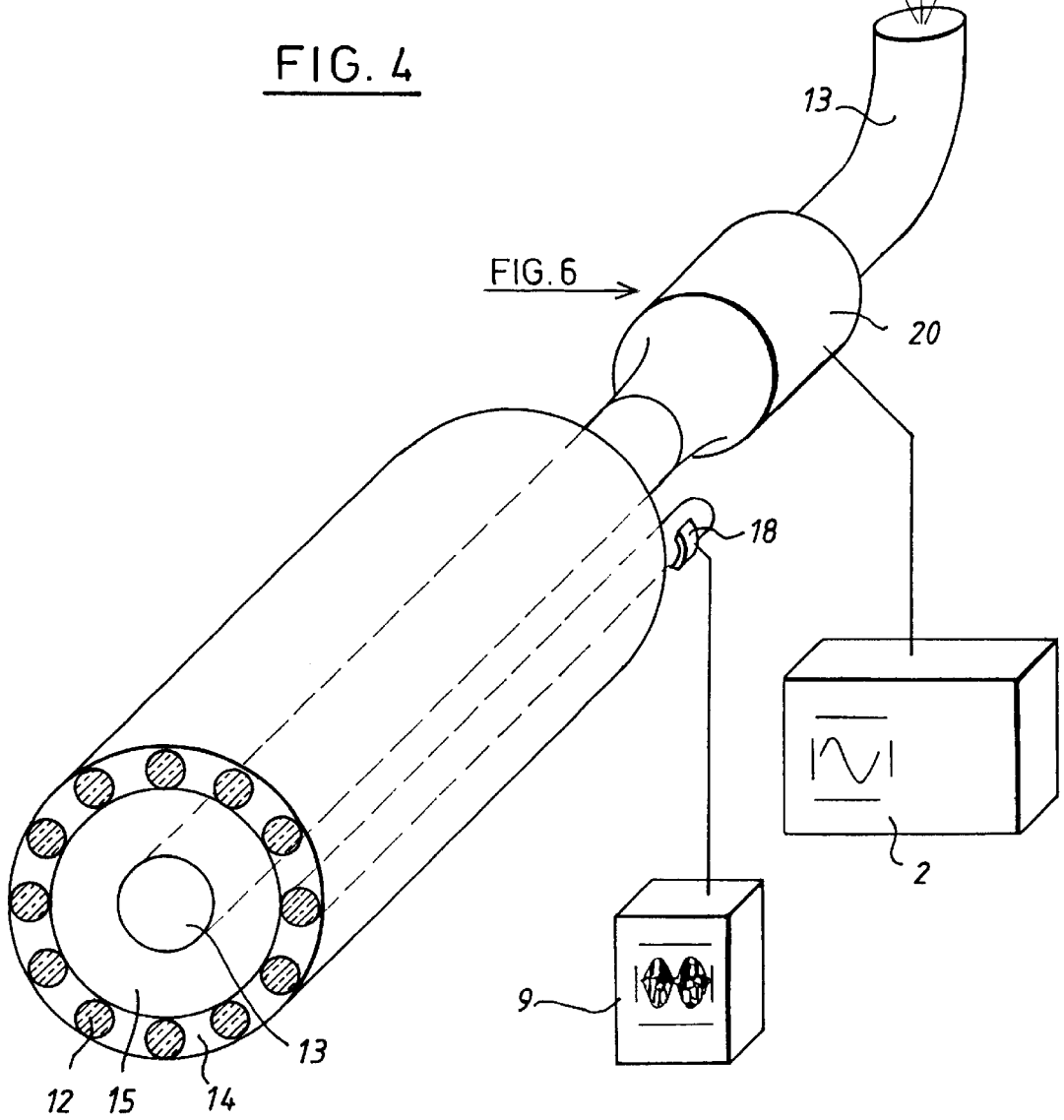
FIG. 4 is a further preferred embodiment of the instrument of the invention.

In FIG. 4, a further preferred embodiment of the instrument of the invention is shown. Here, the ultrasound of the sound head shown in FIG. 6 and the laser radiation of the Nd:YAG-laser 7 are transmitted simultaneously through a central quartz glass fiber 13 onto the proximal end of the waveguide 13. The laser radiation is transmitted after deflection and focusing with the aid of optic 6. To this extent, this portion of the instrument corresponds to the embodiment of FIG. 2. The central waveguide 13 has a diameter of 600 µm.

A so-called multifiber annular catheter 14 is placed about the central quartz glass fiber 13. This annular catheter 14 comprises several light conducting fibers 12 having a small diameter of approximately 50 µm. This annular catheter fiber bundle transmits the higher frequency ultrasound in the range between 1 MHz and 50 MHz for the ultrasound diagnosis. For this purpose, the ends of the fibers 12 are joined at the proximal end, for example, by being joined to each other with adhesive, and a combined ultrasound transmitter/receiver 18 is coupled to this common fiber end. The ultrasonic transmitter/receiver 18 is connected to the diagnostic unit 9 as shown in FIG. 8.

The power ultrasound transmitted by the quartz glass fiber 13 for the therapy lies in the frequency range between 30 kHz and 200 kHz, preferably at approximately 100 kHz.

The annularly-shaped channel between the annular catheter 14 and the central thicker waveguide 13 can serve to transmit the irrigating liquid.

The glass fibers 12 can furthermore be utilized to return transmit optical signals from the distal end of the instrument, for example, fluorescence radiation, which is detected in diffuse reflectance with the aid of photoelectric detectors placed at the proximal end of the fibers 12.

Figure 7:
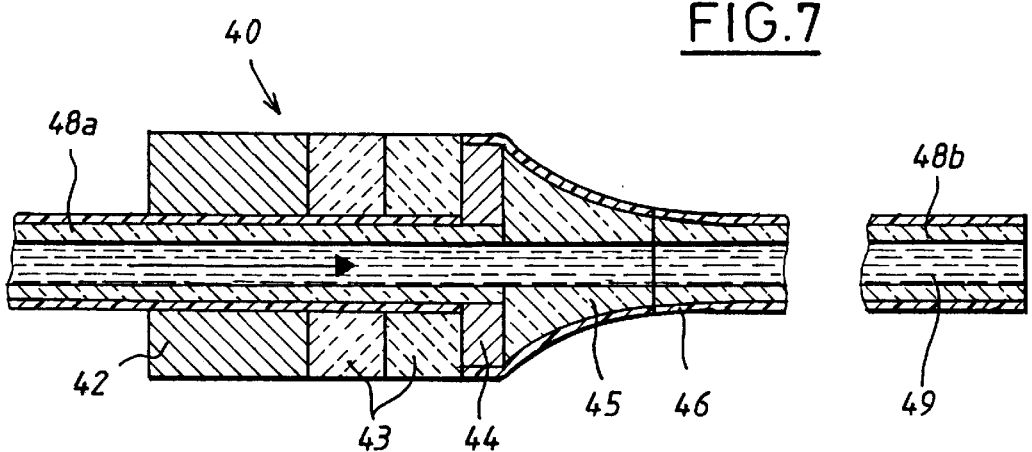
FIG. 7 is a more detailed illustration of a sound head suitable for hollow waveguides.

In the previous embodiments, a quartz glass fiber having a full core has been shown as waveguide for transmitting the power ultrasound for the therapy or for the laser radiation. In lieu of such a fiber, it is however also possible to use a capillary as shown in FIG. 7. There, the waveguide comprises a hollow quartz glass capillary 48. This quartz glass capillary is partitioned in the region of the sound transducer as in the embodiment of FIG. 7. The proximal piece 48a of the hollow waveguide is again inserted in a central bore in the damping element 42 and the piezoceramic discs 43 of the sound transducer. However, the bore here extends through the impedance converter so that the end of this waveguide piece 48a is seated directly on the thicker end of the amplitude transformer 45. The amplitude transformer 45 likewise has a central bore and in the same magnitude as the capillary inner diameter. The second distal piece 48b of the hollow waveguide joins at the amplitude transformer.

In this embodiment, the power ultrasound for the therapy, which is generated by the sound transducer 43, is transmitted by the walls of the quartz glass capillary 48b. A liquid is flushed through the interior 49 for cooling the waveguide. This liquid is transparent for the wavelength of the laser radiation which is to be simultaneously transmitted. The laser radiation is coupled into the liquid core of the waveguide 48a from the proximal end.

Also in this embodiment, 46 identifies again the optical cladding having a lower index of refraction which is intended to prevent exiting of light from the waveguide 48b.

What is claimed is:

1. An instrument for performing invasive and endoscopic work at a work location, the instrument having a proximal end and a distal end and comprising:

an ultrasound source for supplying ultrasound energy provided at or coupled to the proximal end of said instrument and supplying an intensity and frequency of ultrasound at said distal end adequate for cutting tissue;

a laser for supplying light energy and said laser being also coupled to the proximal end of said instrument and providing a laser light intensity in a therapeutic range;

an elongated waveguide for transmitting said ultrasound energy and said laser light energy from the proximal end to the distal end of said instrument;

said elongated waveguide being configured to transmit to said distal end at least 5 W of said ultrasound energy at a frequency of less than 1 MHz; and, said elongated waveguide being made of glass transparent to said light energy and being a single waveguide for guiding both said laser light energy and said ultrasound energy.

2. The instrument of claim 1, wherein said elongated waveguide has a diameter greater than 0.05 mm.

3. The instrument of claim 1, wherein said elongated waveguide is surrounded by a jacket within which a liquid medium is provided which flushes said elongated waveguide.

4. The instrument of claim 1, wherein said ultrasound source is a first ultrasound source and said instrument further comprises a second ultrasound source operating in a frequency range and providing an ultrasound intensity with said frequency range and said intensity both being so selected that the ultrasound of said second ultrasound source is suitable for diagnosing tissue damage; and, said second ultrasound source being operatively connected to said single waveguide so as to permit the ultrasound of said second ultrasound source to be transmitted by said single waveguide.

5. The instrument of claim 4, wherein the ultrasonic power of said second ultrasound source transmitted to said distal end is less than 1 W or the ultrasound energy transmitted to said distal end is less than 100 W cm$^{-2}$ and that the frequency of the ultrasound of said second ultrasound source is greater than 1 MHz.

6. The instrument of claim 4, wherein said elongated waveguide has a diameter of less than 0.1 mm.

7. The instrument of claim 1, wherein said laser is a therapeutic laser and supplies laser radiation at an optical power at said distal end which is at least 5 Watts or at an intensity at said distal end which is at least 1 kW cm$^{-2}$.

8. The instrument of claim 7, wherein the wavelength of said laser radiation is between 300 nm and 3 μm.

9. The instrument of claim 7, wherein the wavelength of said laser radiation is in the near infrared range between 1 μm and 1.5 μm.

10. The instrument of claim 1, further comprising an ultrasonic transmitter/receiver mounted at said proximal end for transmitting and receiving diagnostic ultrasound; and, a plurality of additional waveguides all operatively connected to said ultrasonic transmitter/receiver at said proximal end for transmitting said diagnostic ultrasound between said distal end and said ultrasonic transmitter/receiver at said proximal end.

11. The instrument of claim 10, wherein said elongated waveguide further comprises an inner waveguide; said additional waveguides surround said inner waveguide in a ring-shaped manner; and, said inner waveguide is connected to said ultrasound source and the laser.

12. The instrument of claim 11, wherein said waveguide has a jacket having an index of refraction deviating from that of the fiber core and/or a deviating acoustic impedance.

13. The instrument of claim 1, wherein said ultrasound source has associated therewith a damping member, a sound transducer, an impedance converter and an amplitude transformer preferably in the form of a taper.

14. The instrument of claim 13, wherein said damping member, said sound transducer and said impedance converter are cylindrical components which are placed one against the other and wherein said damping member and said sound transducer are provided with an inner bore in which a light conductor is seated which is connected to said laser source means.

15. The instrument of claim 14, wherein said impedance converter and said amplitude transformer are made of a material transparent for the laser radiation.

* * * * *

UNITED STATES PATENT AND TRADEMARK OFFICE
CERTIFICATE OF CORRECTION

PATENT NO. : 6,238,386 B1
DATED : May 29, 2001
INVENTOR(S) : Gerhard Mueller and Johannes Tschepe Page 1 of 1

It is certified that error appears in the above-identified patent and that said Letters Patent is hereby corrected as shown below:

Column 1,
Line 31, delete "Ubertragung" and substitute -- Übertragung -- therefor.
Line 33, delete "fur" and substitute -- für -- therefor.

Column 2,
Line 41, delete "fur" and substitute -- für -- therefor.

Column 4,
Line 5, delete "PQ".
Line 24, delete "$\lambda/_4$" and substitute -- $\lambda/4$ -- therefor.
Line 38, delete "e" and substitute -- $\epsilon$ -- therefor.
Line 40, delete the "$P_{ATp=\epsilon\ PATd}$" and substitute -- $P_{ATp} = \epsilon\ P_{ATd}$ -- therefor.
Line 47, delete "PIW" and substitute -- $P_{IW}$ -- therefor.
Line 59, delete "$P_{pw}$" and substitute -- $P_{pW}$ -- therefor.

Column 5,
Line 48, delete "dd" and substitute -- $d_d$ -- therefor.

Column 7,
Line 36, delete "13.3 x $10_6$" and substitute -- 13.3 x $10^6$ -- therefor.

Signed and Sealed this

Thirtieth Day of April, 2002

Attest:

JAMES E. ROGAN
*Attesting Officer*          *Director of the United States Patent and Trademark Office*